United States Patent [19]
Pellet et al.

[11] Patent Number: 5,952,233
[45] Date of Patent: Sep. 14, 1999

[54] TEST KIT FOR MEASURING THE LEVEL OF CARBOXYLATE ANION IN ENGINE COOLANT

[75] Inventors: Regis J. Pellet, Croton-on-Hudson; Leonard S. Bartley, Jr., Newburg; Paul M. V. Van de Ven, Fishkill, all of N.Y.

[73] Assignee: Texaco Inc., White Plains, N.Y.

[21] Appl. No.: 09/040,158

[22] Filed: Mar. 17, 1998

Related U.S. Application Data

[62] Division of application No. 08/819,907, Mar. 18, 1997, Pat. No. 5,744,365.

[51] Int. Cl.⁶ ...................................................... G01N 21/78
[52] U.S. Cl. .................................................. 436/6; 422/53
[58] Field of Search .................................... 436/6, 73, 76, 436/79, 164, 177; 422/53, 55, 61

[56] References Cited

U.S. PATENT DOCUMENTS

| | | | |
|---|---|---|---|
| 2,820,016 | 1/1958 | Raifsnider et al. | 436/6 |
| 3,079,343 | 2/1963 | Bernard . | |
| 3,110,567 | 11/1963 | Hughes et al. | 436/6 |
| 3,980,433 | 9/1976 | Tamura et al. | 436/129 |
| 4,647,392 | 3/1987 | Darden et al. | 252/75 |
| 4,657,689 | 4/1987 | Darden | 252/75 |
| 4,777,143 | 10/1988 | Price et al. | 436/129 |
| 4,876,068 | 10/1989 | Castaneda . | |
| 4,894,346 | 1/1990 | Myers et al. | 436/85 |
| 5,085,791 | 2/1992 | Burns | 252/79 |
| 5,085,793 | 2/1992 | Burns et al. | 252/79 |
| 5,242,621 | 9/1993 | Miller et al. | 252/396 |

FOREIGN PATENT DOCUMENTS 0534692  3/1993  European Pat. Off. .

OTHER PUBLICATIONS

Dalal, R.C. "Colorimetric determination of aluminum in soil extracts using haematoxylin" Plant and Soil, vol. 36, pp. 223–231, 1972.

Tarek, M. et al "Use of Haemotoxylin in an Improved Method for the Determination of Ultramicro Amounts of Aluminum" Analyst, vol. 113, pp. 577–580, 1988.

Kokubu, N. "Colorimetric determination of fluoride by the aluminum–hematoxylin method" Chemical Abstracts, vol. 88, abstract No. 83101z, 1978.

Washington, et al. Performance of Organic Acid based Coolants in Heavy Duty Applications; Society of Automotive Engineering, vol. SP, No. SP–1162, 1996, pp. 61–66.

*Primary Examiner*—Jeffrey Snay
*Attorney, Agent, or Firm*—Henry H. Gibson; Dilworth & Barrese

[57] ABSTRACT

A colorimetric method is provided for determining the presence or absence of a corrosion-inhibitory level of carboxylate anion in used aqueous engine coolant.

9 Claims, No Drawings

TEST KIT FOR MEASURING THE LEVEL OF CARBOXYLATE ANION IN ENGINE COOLANT

This is a divisional of application No. 08/819,907 filed Mar. 18, 1997, now U.S. Pat. No. 5,744,365.

BACKGROUND OF THE INVENTION

This invention relates to a method for measuring carboxylate anion present in used automotive and heavy duty engine coolants where it functions as a corrosion inhibitor and to a test kit for carrying out the method.

Automotive engine cooling systems contain a variety of metals and metal alloys such as copper, solder, brass, steel, cast iron, aluminum and magnesium. The vulnerability of such metals to corrosive attack is high due to the presence of corrosive liquids and various ions as well as the high temperatures, pressures and flow rates characteristic of engine cooling systems. The presence of corrosion products within a cooling system can also interfere with heat transfer from the engine combustion chambers which may subsequently cause engine overheating and engine component failure.

Corrosion inhibitors are commonly added to engine coolants, e.g., silicates are added to provide aluminum protection, nitrites are added for cast iron protection and azoles may be added for copper and brass corrosion protection and to assist in the protection of iron and steel. All corrosion inhibitors employed in automotive antifreeze/coolant formulations are gradually depleted by use. The life expectancy of most coolants is about one to three years due to the progressive depletion of the corrosion inhibitor component(s). Carboxylic acids in the form of their salts have been incorporated into engine coolants to provide a greater degree of corrosion protection than other known types of corrosion inhibitors. Carboxylates are superior due to their slower depletion rates compared with other corrosion inhibitors. The life expectancy of carboxylate-containing coolants are typically five years or more.

For proper coolant maintenance, the engine operator should routinely monitor coolant levels to determine that the coolant is providing suitable boil and freeze point protection. To maintain adequate levels of corrosion inhibitor, it is also essential that the engine operator continually monitor corrosion inhibitor levels and replenish the same as the circumstances require. Replacement of the entire coolant may be required when severe deterioration or contamination occurs.

Quick test methods are available for determining corrosion inhibitor contents, e.g., nitrite content, molybdate content, etc., of used engine coolant which involve immersing a test strip in the coolant which produces a color change that can be related to the corrosion inhibitor level. A low reading for the corrosion inhibitor indicates that corrective action should be taken to restore protection, e.g., the use of supplemental coolant additives or extenders to restore specific corrosion inhibitor levels for sufficient protection. Test methods are also available to determine that corrosion inhibitor levels do not become too high when supplemental coolant additives are used to restore corrosion inhibitor levels.

In use, carboxylate corrosion inhibitors deplete at a slower rate than other known inhibitors but, over time, may become contaminated by dilution with other manufactured engine coolants or water following coolant top-off. In order for the carboxylate corrosion inhibitors to provide adequate corrosion protection, their levels in used automotive and heavy duty engine coolants must be periodically determined.

Carboxylate anion present in used engine coolant can be analyzed by a well-equipped laboratory employing chromatographic techniques. However, these procedures are expensive and time consuming. Accordingly, there exists a need for an inexpensive, expeditious and reliable method for determining carboxylate anion levels present in used automotive and heavy duty engine coolants which lends itself to being carried out in the field with a minimum of technical expertise.

SUMMARY OF THE INVENTION

In accordance with the present invention, a method is provided for determining the presence or absence of a corrosion-inhibitory level of carboxylate anion in used engine coolant which comprises:

a) obtaining a known quantity of the engine coolant as a representative sample thereof, the sample containing a level of carboxylate anion to be determined;

b) adding a fixed quantity of a source of aluminum cation to the sample, the aluminum cation complexing with the carboxylate anion to form an insoluble aluminum-carboxylate complex, there being free aluminum cation present in the sample when the level of carboxylate anion therein is below an effective corrosion-inhibitory amount and there being no aluminum cation present in the sample when the level of carboxylate anion is at an effective corrosion-inhibitory amount;

c) adding a color indicator to the sample which forms an irreversibly colored complex with any free aluminum cation present therein at a pH which results in the colored complex, the sample being adjusted to within this pH if necessary to permit the formation of such colored complex; and, d) observing the color of any complex which may have formed between free aluminum cation and the color indicator to determine the level of carboxylate anion in the sample, the sample being adjusted to a different pH if necessary in order to cancel out any color that may have resulted from the presence of excess color indicator in the sample.

Further in accordance with the present invention, a portable test kit, suitable for field use, is provided for conducting the foregoing calorimetric method of determining the level of carboxylate anion in-used automotive and heavy duty engine coolants.

DESCRIPTION OF THE PREFERRED EMBODIMENTS

The corrosion inhibitors whose levels are determined in accordance with the method of this invention are the alkali metal or ammonium salts of carboxylic acids that form a water insoluble aluminum-carboxylate complex upon reaction with a source of aluminum cation. Examples of such alkali metal or ammonium salts are those of suberic acid, azelaic acid, undecanedioic acid, dodecanedioic acid, propionic acid, butyric acid, valeric acid, caproic acid, ethylhexanoic acid, benzoic acid, paratertiary butylbenzoic acid, cyclohexane carboxylic acid, and the like. A preferred carboxylate corrosion inhibitor is an alkali metal ethylhexanoate, e.g., sodium ethylhexanoate, potassium ethylhexanoate, etc.

A known quantity of used automotive or heavy duty engine coolant is withdrawn from the engine cooling system to provide a representative sample whose carboxylate anion content is to be determined. Generally, the amount of the coolant sample can vary from about 2 to about 100 g and preferably from about 5 to about 30 g. A fixed quantity of a source of aluminum cation, e.g., an aluminum cation stock solution, is then added to the sample. The precise quantity of aluminum cation will depend upon the size of the coolant sample and the mole percent of carboxylate anion required for adequate corrosion protection. Routine testing can be carried out to provide stock solutions of suitable aluminum cation concentration for particular coolant formulations. Suitable sources of aluminum cation for preparing such stock solutions include soluble aluminum compounds such as the chlorides, sulfates, nitrates, etc., of aluminum and their hydrates. Aluminum nitrate nonahydrate, $Al(NO_3)_3 \cdot 9H_2O$, has been found to provide especially good results.

Following the addition of aluminum cation, the aluminum cation complexes with carboxylate anion to produce an insoluble aluminum-carboxylate complex. The carboxylate anion content of the coolant sample will determine the amount of aluminum-carboxylate complex that is formed. When the carboxylate anion content has fallen below a predetermined corrosion-inhibitory effective amount, i.e., the situation that results from excessive depletion of carboxylate anion over time, the entire amount of carboxylate anion in the sample will complex with the aluminum cation and some free aluminum cation will remain in the sample. The amount of free aluminum cation present in the sample is inversely related to its carboxylate anion content such that when there is a corrosion-inhibitory effective level of carboxylate anion, there will be no free aluminum cation present in the coolant sample and conversely, when there is insufficient carboxylate anion to provide a predetermined level of corrosion inhibition, there will be free aluminum cation present in the sample. Thus, when the content of carboxylate anion in the coolant sample is at a corrosion-inhibitory effective level, the entire amount of added aluminum cation will complex with the carboxylate anion with no free aluminum cation remaining in the sample. However, when the carboxylate anion content has fallen below some predetermined level, there will be some amount of free aluminum cation present in the sample.

Following formation of the insoluble aluminum-carboxylate complex, the sample is optionally filtered to remove the particles of insoluble complex thus providing a clear-sample free of any suspended particles of insoluble complex that might tend to obscure the color change that occurs when, as described below, a color indicator is added to the sample. While other techniques can be used to remove the insoluble aluminum-carboxylate complex, e.g., centrifugation followed by decantation of the resulting clear liquid, filtration is a simple procedure requiring a minimum of equipment and as such well adapted for field use.

Once the insoluble aluminum-carboxylate complex has been formed (and optionally separated from the coolant sample as previously discussed), a color indicator that complexes with aluminum cation is added to the sample. If there is free aluminum cation present in the sample which, as explained above, will be the case when the carboxylate content of the sample is below a predetermined corrosion inhibitory effective amount, the color indicator will form an irreversibly colored complex with the aluminum cation. If, however, there is no free aluminum cation present in the sample, as when the carboxylate anion content is at a predetermined minimum corrosion inhibitory effective level, addition of color indicator will not result in the formation of any aluminum-color indicator complex.

Suitable color indicators that can be used herein are well known to those skilled in the art and include hematoxylin, Eriochrome Cyanine R, aurintricarboxylic acid, Pantachrome Blue Black R, Alizarin S, and the like. Hematoxylin produces clearly observable color changes when complexed with aluminum cations at an alkaline pH and is preferred for use herein. The concentration of color indicator in the coolant sample can vary according to the type of engine coolant being tested. For example, in the case of hematoxylin, if the coolant does not contain a dye component, then the concentration of hematoxylin will ordinarily range from about 0.005 to about 0.2 mg per g coolant and preferably from about 0.1 to about 0.15 mg per g coolant. If the engine coolant contains a dye component, then the amount of color indicator must be increased due to the interference of the engine coolant dye component with the color resulting from complexing of the color indicator with any free aluminum cations. The increased concentration of color indicator will ordinarily range from about 0.2 to about 0.8 mg per g coolant and preferably from about 0.4 to about 0.6 mg per g coolant.

As previously noted, hematoxylin forms an irreversibly colored complex with aluminum cation only at alkaline pH. Accordingly, it may be necessary to adjust the pH of the sample with a base, e.g., to a pH greater than 7 and preferably to a pH of at least about 8 before or after addition of the color indicator. Since excess hematoxylin will itself produce color at alkaline pH, it may be necessary to acidify the coolant sample once the aluminum-color indicator complex has formed in order to cancel out or neutralize any color that may be due to the presence of excess hematoxylin. Since the color change in the sample which was brought about by the formation of the aluminum-color indicator complex is irreversible, the subsequent acidification of the sample will not affect a change in the color of the color indicator-aluminum complex but will only cancel out the color that had been produced by the presence of excess hematoxylin at the previous alkaline pH.

When complexed with aluminum cations and at alkaline pH, hematoxylin gives a clearly observed purple color. If, following acidification of the sample, the purple color is absent (as will be the case when there is no free aluminum cation therein), it can be concluded that the carboxylate anion is present in the coolant in at least a predetermined minimum corrosion inhibitory amount. However, when the purple color is observed (as will be the case when an aluminum-color indicator complex has formed), it can be concluded that the level of carboxylate anion in the coolant has fallen below a predetermined corrosion inhibitory effective amount and must be replenished.

It is further within the scope of the invention to provide a kit containing the apparatus and/or reagents necessary to carry out the foregoing test method in the field. A complete kit would contain all of the equipment and consumables for conducting at least one test procedure. Thus, such a kit would include a device for obtaining a test sample of coolant, e.g., a pipette or syringe for drawing coolant, at least one device for holding a precise volume of coolant liquid, e.g., a flask or column, a source of aluminum cation, e.g., one of aluminum nitrate, preferably provided as a stock solution, and a color indicator. Where the color indicator is hematoxylin or other indicator that produces color only at alkaline pH, the kit would also contain a quantity of base with which to adjust the pH of the coolant sample to within the alkaline region and a quantity of acid with which to readjust the pH of the coolant sample to cancel out any color resulting from the presence of excess color indicator.

Optionally, the kit can contain a filtration device, e.g., a funnel and filter paper, to separate suspended particles from the coolant sample following formation of the insoluble aluminum-carboxylate complex. A partial test kit would include, at a minimum, the aforesaid source of aluminum cation and color indicator.

The following examples are illustrative of the method of this invention.

EXAMPLE 1

This example illustrates the reproducible nature of the reaction of aluminum cation and ethylhexanoate anion over a range of solution compositions.

A stock solution of aluminum cation, $Al^{+3}$, was prepared by dissolving 3.006 g of aluminum nitrate nonahydrate $(Al(NO_3)_3 \cdot 9H_2O)$ in 147.5 g of deionized water. Five additional mixtures were prepared by adding aliquots of a modified Havoline Extended Life AntiFreeze/Coolant (Coolant A) to the aluminum stock solutions and diluting with deionized water. The Coolant A formulation used in this example was identical to the commercially available Havoline Extended Life Antifreeze/coolant available from Texaco Lubricant Company except that it did not contain any antifoamant and dye components. Coolant A was formulated with ethylhexanoic acid which converted in situ in the presence of the potassium hydroxide component to form potassium ethylhexanoate, the active corrosion inhibitor. The partial composition of Coolant A is set forth in Table 1 as follows:

TABLE 1

Coolant A Composition

| Component | Amount, Weight % |
|---|---|
| potassium ethylhexanoate | 3.26* |
| dye | — |
| antifoamant | — |

*As ethylhexanoic acid; present in ethylene glycol.

The overall composition of the Aluminum-Coolant A mixtures are as follows:

TABLE 2

Aluminum-Coolant A Mixtures

| Mixture No. | Weight of Al Stock Solutions, (g) | Weight of Coolant A, (g) | Weight of Deionized Water, (g) |
|---|---|---|---|
| 1 | 20.0 | 9.5 | 20.5 |
| 2 | 20.0 | 7.6 | 22.4 |
| 3 | 20.0 | 6.7 | 23.4 |
| 4 | 20.0 | 5.7 | 24.3 |
| 5 | 20.1 | 4.8 | 25.3 |

For all five mixtures, an aluminum-ethylhexanoate precipitate was observed to have formed. All of the mixtures were then filtered to remove the precipitate and were analyzed for aluminum and ethylhexanoate content. Table 2 summarizes the elemental compositions of each aluminum-ethylhexanoate solution as calculated based on components added (initial composition) and as measured by analysis following the aluminum cation (Al) and ethylhexanoate anion (EH) reaction (final composition).

TABLE 3

Aluminum and Ethylhexanoate Concentrations (moles/liter) Before and After Reaction and Filtration

| Solution | Initial Al | Initial EH | Final Al | Final EH | Change in Al | Change in EH | Change Mole Ratio EH/Al |
|---|---|---|---|---|---|---|---|
| 1 | 0.0213 | 0.0428 | 0 | <0.007 | 0.0213 | >0.0358 | >1.67 |
| 2 | 0.0213 | 0.0341 | 0.00204 | 0 | 0.01926 | 0.0341 | 1.771 |
| 3 | 0.0213 | 0.0298 | 0.00407 | 0 | 0.01723 | 0.0298 | 1.73 |
| 4 | 0.0213 | 0.0256 | 0.00641 | 0 | 0.01489 | 0.0256 | 1.72 |
| 5 | 0.0213 | 0.0213 | 0.00930 | 0 | 0.012 | 0.0213 | 1.775 |

From the results listed in Table 3, it is shown that the amount of ethylhexanoate anion that reacts with aluminum cation is constant as indicated by the change in molar ratio EH/Al and averages about 1.75 moles of ethylhexanoate anion consumed for every mole of aluminum cation consumed for Solution Nos. 2–5. For Solution No. 1, the EH concentration was too low for accurate measurement. Thus, over a wide range of coolant concentrations the stoichiometry of aluminum and EH reaction remain constant.

$$Al + 1.75 EH \rightarrow Al(EH)_{1.75} \qquad (1)$$

Based on this stoichiometry, it is possible to predict within experimental error, the composition of the final reaction mixture if the amounts of aluminum cation and ethylhexanoate anion in the initial mixture are known.

$$Al_{final} = Al_{initial} - (EH_{initial}/1.75) \qquad (2)$$

Table 4 below presents the results for hypothetical mixtures of equal volumes of aluminum cation and ethylhexanoate anion solutions.

TABLE 4

Predicted Compositions Resulting From Reaction of Aluminum Cation Solution with Varying Ethylhexanoate Anion Solutions

| Target Molar Ratio: EH/Al | Initial Al Cation Conc. (moles/liter) | Initial EH Concentration (moles/liter) | Predicted Final Al Cation Conc. (moles/liter) |
|---|---|---|---|
| 5.0 | 1.0 | 5.0 | 0.0 |
| 3.0 | 1.0 | 3.0 | 0.0 |
| 2.0 | 1.0 | 2.0 | 0.0 |
| 1.6 | 1.0 | 1.6 | 0.09 |
| 1.4 | 1.0 | 1.4 | 0.20 |
| 1.2 | 1.0 | 1.2 | 0.31 |
| 1.0 | 1.0 | 1.0 | 0.43 |
| 0.0 | 1.0 | 0.0 | 1.0 |

Thus, when the initial ethylhexanoate anion concentration is less than 1.75 moles/liter, free aluminum cation will be present in the final reaction mixture. In this example, an initial aluminum ion concentration of 1 was arbitrarily selected. In practice the initial aluminum cation concentration can be chosen such that aluminum cation will be present in the final solution when the initial ethylhexanoate anion concentration falls below a minimum value needed to provide adequate corrosion protection. In this latter case, the presence of aluminum cation in the final reaction mixture would indicate that the level of corrosion protection was insufficient. The stoichiometry of the reaction of aluminum cation with ethylyhexanoate anion may vary with other ethylhexanoate-containing coolants. In such a case, the minimum amount of aluminum cation needed to determine a minimum ethylhexanoate anion content will also vary and must be determined empirically.

EXAMPLE 2

This example illustrates the method of the invention for determining the presence or absence of effective levels of ethylhexanoate anion in various coolant solutions.

Five solutions were prepared by combining the indicated amounts of aluminum cation stock solution with Coolant A as described in Example 1. The solutions were combined so that the resultant mixtures contained ethylhexanoate anion and aluminum cations in ratios ranging from 5 to 0. Table 5 presents the exact proportions of the components used to prepare each solution.

TABLE 5

Aluminum and Coolant A Solution Ratios

| Solution | Target Molar Ratio EH/Al | Weight of Al Cation Stock Solutions, (g) | Weight of Coolant A, (g) | Weight of Deionized Water, (g) |
|---|---|---|---|---|
| 1 | 5.0 | 20.0 | 23.7 | 6.4 |
| 2 | 3.0 | 20.0 | 14.3 | 15.8 |
| 3 | 2.0 | 20.0 | 9.5 | 20.5 |
| 4 | 1.0 | 20.0 | 4.8 | 25.3 |
| 5 | 0.0 | 20.0 | 0.0 | 30.1 |

To determine the presence or absence of free aluminum cation following the mixture and reaction of the components of the solutions listed in Table 5, a calorimetric test for aluminum was adapted from a procedure described in Hattfield, W. D., "Soluble Aluminum and Hematoxylin Test in Filtered Waters." *Ind. and Egn. Chem.*, March 1924, p. 233. In accordance with this procedure, aqueous aluminum cations produce a purple color in the presence of hematoxylin as color indicator. The test is reported to be sensitive to aluminum cations in concentrations within the ppb range. If no aluminum cations are present, the hematoxylin indicator produces a yellow color under the conditions of this test.

Each solution in Table 5 was rendered alkaline with 1.0 g of a saturated solution of ammonium carbonate in deionized water. 1.0 g of color indicator solution (0.1 g hematoxylin in 100 g of deionized water) was then added to each solution shown in Table 5. The resulting mixtures were agitated and allowed to stand for 15 minutes to permit reaction of the color indicator with the free aluminum cations if present. Next, each solution was acidified to a pH of about 5 by the addition of 10 g of 30% acetic acid and filtered to remove the aluminum ethylhexanoate precipitate which formed when the aluminum stock solution was initially mixed with Coolant A. Table 6 below presents the observed color changes in the resulting filtrates:

TABLE 6

Filtrate Colors following Hematoxylin Test for Free $Al^{+3}$ in Coolant A Solutions (Molar Ratio EH/Al = 5 to 0)

| Filtrate | Color |
|---|---|
| 1 | Yellow (color unchanged) |
| 2 | Yellow (color unchanged) |
| 3 | Yellow (color unchanged) |
| 4 | Dark Purple |
| 5 | Dark Purple |

These results indicated that there was no free aluminum cation present in Filtrate Nos. 1, 2 and 3 but free aluminum cation was present in Filtrate Nos. 4 and 5. Furthermore, the results indicate that there was sufficient ethylhexanoate in original Mixture Nos. 1, 2 and 3 to entirely remove all of the aluminum cation added to those mixtures but in Mixture Nos. 4 and 5, there was insufficient ethylhexanoate present to completely react with all of the added aluminum cation.

To further define the sensitivity of the test to varying aluminum cation content and to ethylhexanoate anion content, an additional five reaction solutions were prepared possessing starting molar ratios EH/Al ranging from 2.0 to 1.0. Table 7 presents the amount of each component used to prepare the five solutions.

TABLE 7

Aluminum and Coolant A Solution Ratios

| Solution | Target Molar Ratio EH/Al | Weight of Al Cation Stock Solutions, (g) | Weight of Coolant A, (g) | Weight of Deionized Water, (g) |
|---|---|---|---|---|
| 1 | 2.0 | 20.0 | 9.6 | 20.5 |
| 2 | 1.6 | 20.0 | 7.7 | 22.4 |
| 3 | 1.4 | 20.0 | 6.7 | 23.4 |
| 4 | 1.2 | 20.0 | 5.8 | 24.3 |
| 5 | 1.0 | 20.0 | 4.9 | 25.4 |

As with the solutions described in Table 5, each solution was buffered with ammonium carbonate solution, treated with hematoxylin indicator solution and allowed to stand for 15 minutes before acidification and filtration. After filtration, the following colors of the resulting filtrates were observed:

TABLE 8

Filtrate Colors following Hematoxylin Color Test for Free $Al^{+3}$ in Coolant A Solution Mixtures (Molar Ratio EH/Al = 2 to 1)

| Filtrate | Color |
|---|---|
| 1 | Yellow (color unchanged) |
| 2 | Light Purple |
| 3 | Purple |
| 4 | Dark Purple |
| 5 | Dark Purple |

The results in Table 8 show that Filtrate No. 1 was yellow but Filtrate Nos. 2, 3, 4 and 5 exhibited increasing purple coloration indicating the presence of free aluminum cation in all of these solutions with aluminum concentrations rising as the molar ratio EH/Al decreased from 1.6 to 1.0 over the series. The test indicated that with the filtrate from Solution No. 1 in Table 7 (molar ratio EH/Al=2), sufficient ethylhexanoate anion had been added to the original solution to completely deplete all added aluminum cations. For each of the other filtrates, insufficient ethylhexanoate anion had been added to completely remove all of the added aluminum cation. From the color variations across the series, it can be concluded that as the ethylhexanoate anion concentration was reduced, the aluminum cation concentration was proportionately increased.

The results shown in Tables 6 and 8 are summarized in Table 9 as follows:

TABLE 9

Summary: Hematoxylin Color Test
Results on Aluminum Cation and Coolant A Mixtures

| Target Molar Ratio EH/Al | Predicted Final Al Concentration (moles/l) (From Table 3) | Filtrate Color following Hematoxylin Test |
| --- | --- | --- |
| 5.0 | 0.0 | Yellow |
| 3.0 | 0.0 | Yellow |
| 2.0 | 0.0 | Yellow |
| 1.6 | 0.09 | Light Purple |
| 1.4 | 0.20 | Purple |
| 1.2 | 0.31 | Dark Purple |
| 1.0 | 0.43 | Dark Purple |
| 0.0 | 1.0 | Dark Purple |

As shown by comparing Table 9 with the predicted compositions listed in Table 4, there is agreement of the predicted presence of aluminum cation based on the demonstrated stoichiometry of the aluminum-ethylhexanoate reaction with the observed purple color change indicating the presence of aluminum cation.

EXAMPLE 3

This example illustrates the calorimetric test for determining ethylhexanoate level carried out upon Havoline Extended Life Antifreeze/Coolant (Coolant B) commercially available coolant from Texaco Lubricant Company. The partial composition of Coolant B is set forth in Table 10 as follows:

TABLE 10

Coolant B Composition

| Component | Amount, Weight % |
| --- | --- |
| potassium ethylhexanoate | 3.26* |
| dye | 0.10* |
| antifoamant | 0.06* |

*As ethylhexanoic acid; present in ethylene glycol.

Unlike Coolant A used in Examples 1 and 2, Coolant B contains conventional antifoamant and dye components in addition to ethylhexanoate corrosion inhibitor. The dyes present in Coolant B will interfere with the interaction of the hematoxylin indicator with free aluminum cation. This interference tends to obscure the development of the purple color of the aluminum-hematoxylin complex relied upon to indicate the presence of free aluminum cation. This example demonstrates that such dye interference can be overcome by increasing the concentration of color indicator over that used in Example 2.

Four mixtures were prepared using 2% aluminum nitrate stock solutions, Coolant B, water and ammonium carbonate solution, all of which have been discussed hereinabove, with hematoxylin color indicator solutions prepared at higher concentrations. The color indicator solutions were prepared to contain from 5–10 times the hematoxylin indicator content of the solutions used in Example 2. The compositions of the four mixtures are presented in Table 11.

TABLE 11

Colorimetric Test Solutions for
Ethylhexanoate Anion Level in Coolant B

| Mixture | Al Stock Solution | DEX-COOL, (g) | Deionized Water, (g) | Buffer, (g) | Indicator Solution, (g) |
| --- | --- | --- | --- | --- | --- |
| 1 | 10.0 | 2.5 | 12.5 | 1.0 | 0.5 |
| 2 | 10.0 | 5.0 | 10.0 | 1.0 | 0.5 |
| 3 | 10.0 | 2.5 | 12.5 | 1.0 | 1.0 |
| 4 | 10.0 | 5.0 | 10.0 | 1.0 | 1.0 |

Mixture Nos. 1 and 2 were prepared using five times the color indicator, and Mixture Nos. 3 and 4 were prepared using ten times the color indicator, as that used in Example 2. Mixture Nos. 2 and 4 were prepared with an EH/Al molar ratio of 2.1. Since these mixtures contain ethylhexanoate anion in excess of the 1.75 reaction stoichiometry described in Examples 1 and 2, these two solutions will not contain any free aluminum cation after reaction. Mixture Nos. 1 and 3 were prepared with an EH/Al molar ratio of 1.05. These two mixtures contain insufficient ethylhexanoate anion to completely react with all of the aluminum cation added.

The mixtures were allowed to stand for 15 minutes after preparation and then filtered. The color of the resulting filtrates is given in Table 12.

TABLE 12

Effect of Hematoxylin Concentration
of Colorimetric Test Appearance

| Filtrate | Color |
| --- | --- |
| 1 | Purple |
| 2 | Orange |
| 3 | Purple |
| 4 | Rose |

These results show that Filtrate Nos. 1 and 3, containing less than the stoichiometric amount of ethylhexanoate anion needed to completely react with and remove all of the added aluminum cation, gave a positive purple color for aluminum. Filtrate Nos. 2 and 4, containing ethylhexanoate anion in excess of that needed to completely remove all added aluminum cation from solution, gave a negative (non-purple) test. However, unlike the negative aluminum test presented in Tables 6 and 8 which were yellow, these negative tests exhibited colors ranging from orange to rose. This coloration was due to the increased color indicator content of the filtrate and the dyes present in Coolant B. Even with the increased color indicator content and the dyes, the purple color of the positive tests can clearly be distinguished from the negative test colors.

What is claimed is:

1. A test kit for determining the presence or absence of a corrosion-inhibitory level of carboxylate anion in a representative sample of used engine coolant which comprises a source of aluminum cation and a color indicator which forms an irreversibly colored complex with any free aluminum cation in the sample, wherein said source of aluminum cation is selected such that free aluminum cation will be present in a sample only when there is insufficient carboxylate anion present to provide a predetermined level of corrosion inhibition.

2. The kit of claim 1 wherein the source of aluminum cation is selected from the group consisting of aluminum chloride, aluminum sulfate, aluminum nitrate and their hydrates.

3. The kit of claim 1 further comprising a quantity of base and/or acid with which to adjust the pH of the coolant sample.

4. The kit of claim 1 wherein the color indicator is selected from the group consisting of hematoxylin, Eriochrome Cyanine R, aurintricarboxylic acid, Pantachrome Blue Black R and Alizarin S.

5. The kit of claim 4 further comprising a quantity of base and/or acid with which to adjust the pH of the coolant sample.

6. The kit of claim 1 further comprising a device for obtaining a sample of engine coolant and a device for holding a precise volume of the coolant.

7. The kit of claim 6 wherein the device for obtaining a sample of engine coolant is a pipette or syringe.

8. The kit of claim 6 further comprising a filtration unit.

9. The kit of claim 8 wherein the device for obtaining a sample of engine coolant is a pipette or syringe.

\* \* \* \* \*